(12) United States Patent
Wasson et al.

(10) Patent No.: US 8,512,456 B2
(45) Date of Patent: Aug. 20, 2013

(54) OVEN FOR USE IN A GAS CHROMATOGRAPH

(75) Inventors: John G. Wasson, Ft. Collins, CO (US); Robert J. Wasson, Ft. Collins, CO (US)

(73) Assignee: Wasson-ECE Instrumentation, Inc., Ft. Collins, CO (US)

( * ) Notice: Subject to any disclaimer, the term of this patent is extended or adjusted under 35 U.S.C. 154(b) by 330 days.

(21) Appl. No.: 13/023,016

(22) Filed: Feb. 8, 2011

(65) Prior Publication Data

US 2012/0199108 A1 Aug. 9, 2012

(51) Int. Cl.
*G01N 30/02* (2006.01)

(52) U.S. Cl.
USPC ................................... 96/101; 95/87

(58) Field of Classification Search
CPC G01N 30/30; G01N 2030/3084; G01N 30/02
USPC ....... 95/82, 87; 96/101, 102, 103; 73/23.35, 73/23.42
See application file for complete search history.

(56) References Cited

U.S. PATENT DOCUMENTS

| 3,422,603 | A | * | 1/1969 | Redmond, Jr. .................. 96/103 |
| 4,286,456 | A | * | 9/1981 | Sisti et al. .................... 73/23.25 |
| 4,420,679 | A | | 12/1983 | Howe |
| 4,771,628 | A | * | 9/1988 | Sisti et al. .................... 73/23.25 |
| 5,807,426 | A | * | 9/1998 | Ohtsuki et al. ................. 96/102 |
| 5,942,675 | A | | 8/1999 | Wilson |
| 6,248,158 | B1 | * | 6/2001 | Abdel-Rahman et al. ...... 96/101 |
| 6,485,543 | B1 | | 11/2002 | MacDonald et al. |
| 2003/0037592 | A1 | * | 2/2003 | D'Couto et al. ............. 73/23.35 |

* cited by examiner

*Primary Examiner* — Robert Clemente (74) *Attorney, Agent, or Firm* — Christopher J. Kulish (57) ABSTRACT

The invention is directed to an oven for use in gas chromatography. In one embodiment, the oven is comprised of a housing that defines an interior chamber within which a substantial portion of a heating element and a radial fan blade are located. The interior chamber also defines a space within which a separation column is located when the oven is in use. The substantial portion of the heating element is located so as to receive air, when the oven is in operation, that is being moved by the radial fan blade in a direction that is substantially perpendicular to the axis of rotation of the blade. The space within which a separation column is located is also defined so as to receive air, when the oven is in operation, that is being moved by the radial fan blade in a direction that is substantially perpendicular to the axis of rotation of the blade.

20 Claims, 10 Drawing Sheets

OVEN FOR USE IN A GAS CHROMATOGRAPH

FIELD OF THE INVENTION

The present invention is directed to an oven for use in a gas chromatograph.

BACKGROUND OF THE INVENTION

Figure 1:
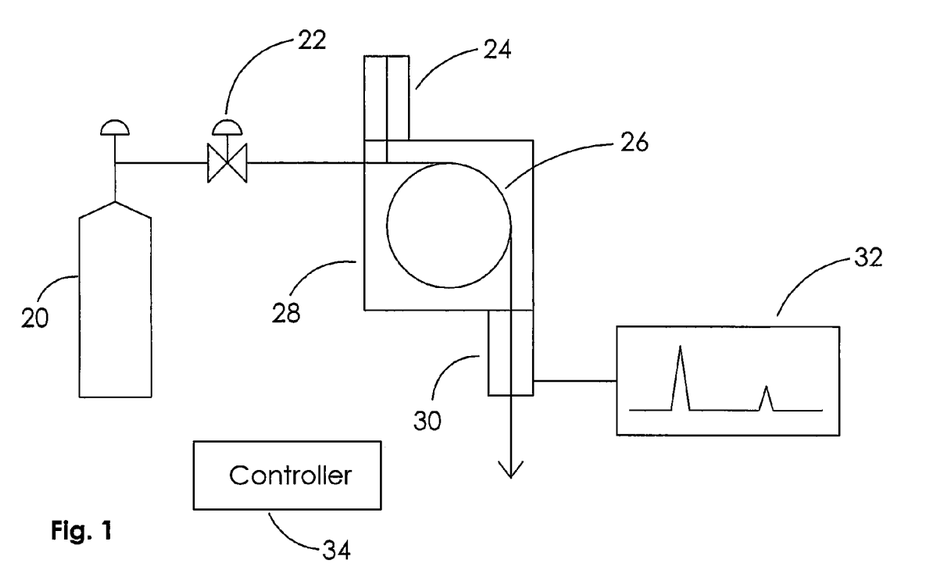
FIG. 1 is a block diagram of a typical gas chromatograph.

With reference to FIG. 1, a gas chromatograph is typically comprised of: (a) a supply of a carrier gas 20; (b) a carrier gas flow controller 22, (c) a sample injection port 24 that allows a sample of unknown or uncertain composition to be injected into a stream of the carrier gas, (d) a separation column 26 for receiving a carrier gas and a sample borne by the carrier gas, (e) an oven 28 for heating a sample being borne by a carrier gas and passing through the separation column, (e) a detector 30 for identifying one or more components of the sample, (f) a recorder 32 for recording the results produced by the detector, and (g) a controller 34 for coordinating the operation of other elements of the gas chromatograph, including the temperature profile to which a sample that is passing through the separation column is subjected.

The separation column is a long, tubular structure that has the desired size exclusion, chemical affinity, or other characteristic or combination of characteristics that cause the structure to provide different degrees of retention to the various chemical analytes as they are pushed along the column and towards the detector. The tubular separation column is typically comprised of three sections—an inlet section that initially receives the carrier gas and sample, a wound section that receives the carrier gas and sample from the inlet section and constitutes the bulk of the length of the column, and an outlet section that receives the carrier gas and sample from the helically wound section. The wound section typically is in the form of a circular helix. Typically, the ends of the column associated with the inlet and outlet sections each have a coupling element that allows the column to be attached to and detached from the carrier gas circuit. This allows columns with different characteristics to be used in the chromatograph.

A typical oven for use in gas chromatography is comprised of: (a) a housing that defines an interior chamber, (b) a heating element located in the chamber and that is used to heat the air in the chamber, the heated air then being used to heat a sample that is passing through a separation column located in the interior chamber, (c) a fan blade that is located in the interior chamber and used to circulate the heated air, (d) a device for positioning a separation column in the interior chamber, (e) a vent system for use in regulating the passage of air into and out of the interior chamber to facilitate a desired air temperature within the interior chamber, and (f) a temperature sensor for sensing the air temperature within the interior chamber. The housing is typically made of sheet metal, with the surface of the sheet metal defining the interior chamber, and a thick inorganic blanket that covers all or a substantial portion of the sheet metal and operates to deter heat transfer from the oven to the ambient atmosphere. Since the separation column for use in the analysis of one sample may not be appropriate for the analysis of another sample, the housing typically incorporates a door that allows a separation column located in the oven to be removed and replaced with another separation column. The vent system operates to prevent ambient air from entering the chamber when the air in the chamber is being heated and allow ambient air into the chamber when cooler air in the chamber is desired.

SUMMARY OF THE INVENTION

The invention is directed to an oven for use in a gas chromatograph that is more efficient in transferring heat to a separation column and any sample passing through the column. In one embodiment, the oven is comprised of a housing that defines an interior chamber, a radial fan, a heating element, and separation column mount. The radial fan is comprised of an electric motor, a drive shaft that is operatively connected to or part of the motor, and a fan blade that is operatively connected to the drive shaft. The fan blade and at least a portion of the drive shaft are located within the chamber. In operation, the fan blade pushes air in a direction that is substantially perpendicular to the drive shaft. A substantial portion of the heating element is positioned to receive, during operation, air that is being pushed by the fan blade in a direction substantially perpendicular to the drive shaft. The separation column mount operates to position a separation column so that, during operation, a substantial portion of the column receives air that is being pushed by the fan blade in a direction that is substantially perpendicular to the drive shaft. As such, the air flow between the noted portions of the heating element and the separation column is substantially perpendicular to the drive shaft of the radial fan. This arrangement of the fan blade, heating element, and separation column mount allows the chamber of the oven to have a significantly smaller volume than known chromatographic ovens. The smaller volume means that there is less air in the chamber to heat than in other ovens. As such, the air can be heated to a desired temperature faster, everything else being equal, than would otherwise be possible. This, in turn, means that a sample passing through the separation column can be subjected to a temperature profile having a steeper rise time.

Further, in an embodiment in which the substantial portion of the heating element is located between the fan blade and the location at which the mount holds the substantial portion of the separation column, the need for any structure that would diminish the heat transfer from the air to the separation column can be substantially reduced and potentially eliminated, thereby resulting in a more efficient heat transfer from the heating element to the column and entrained sample.

In a further embodiment, the oven employs a housing with an interior surface that defines an interior chamber and includes a curved side surface for receiving, when in operation, air that is being driven by the radial fan in a direction substantially perpendicular to the drive shaft. The curved side surface promotes the circulation of air back towards the input portion of the fan blade, i.e., the portion of the fan blade that receives a flow of air, as opposed to the portion of the blade from which air is pushed. Further, the curved side surface is made of a refractory material that has a low heat transfer coefficient, thereby focusing heat transfer on the separation column. In another embodiment, the interior surface is comprised of a circulation flow surface that defines the primary circulation of air between the output portion of the fan blade and the input portion of the fan blade. The circulation flow surface is made of a refractory material with a low heat transfer coefficient to focus heat flow from the heated air to the separation column. In yet a further, embodiment, the entire interior surface of the housing is made of a refractory material to promote heat transfer from the air to the separation column and not the housing.

DETAILED DESCRIPTION

With reference to FIGS. 2, 3A-3D, 4, 5, and 6, an embodiment of an oven according to the present invention, hereinafter referred to as oven 50, is described. Generally, the oven 50 is comprised of a housing 52 for providing an interior chamber for facilitating heat transfer to a sample entrained within a carrier gas traveling through a separation column, a radial fan 54, a heating element 56 for producing the heat that is transferred to the sample, and a separation column mount 58 for positioning a separation column within the chamber.

Figure 2:
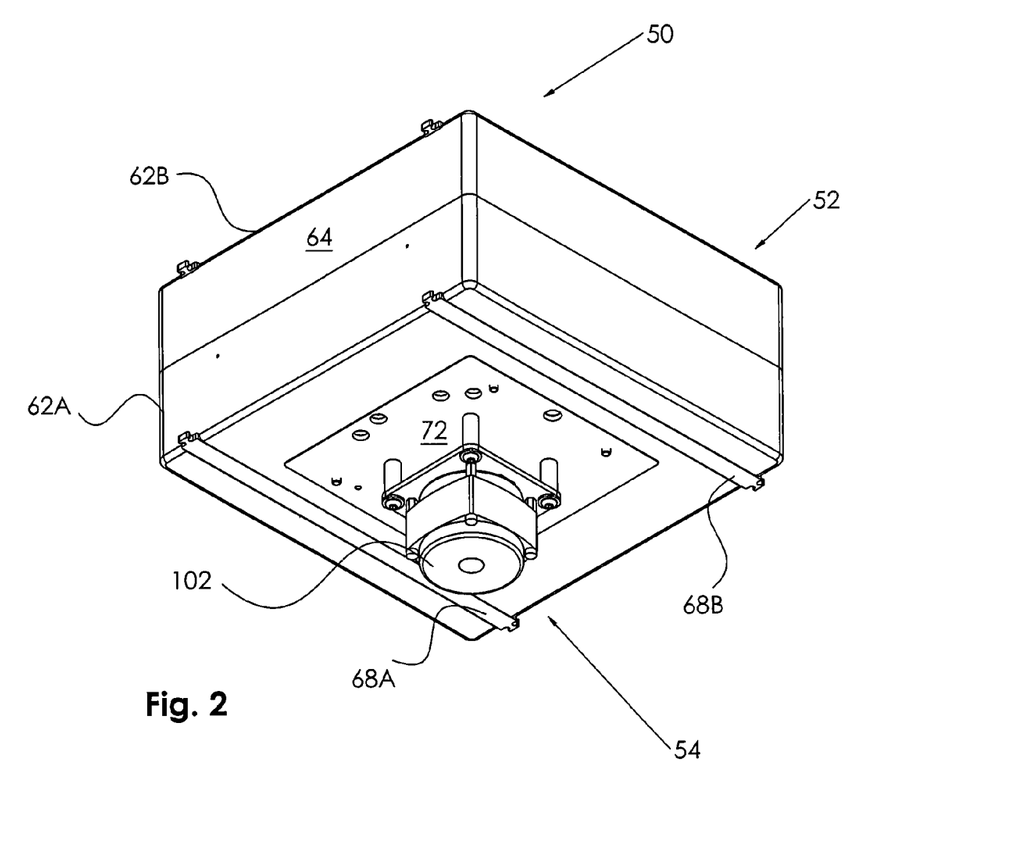
FIG. 2 is a perspective view of an embodiment of the oven.
Figure 3A:
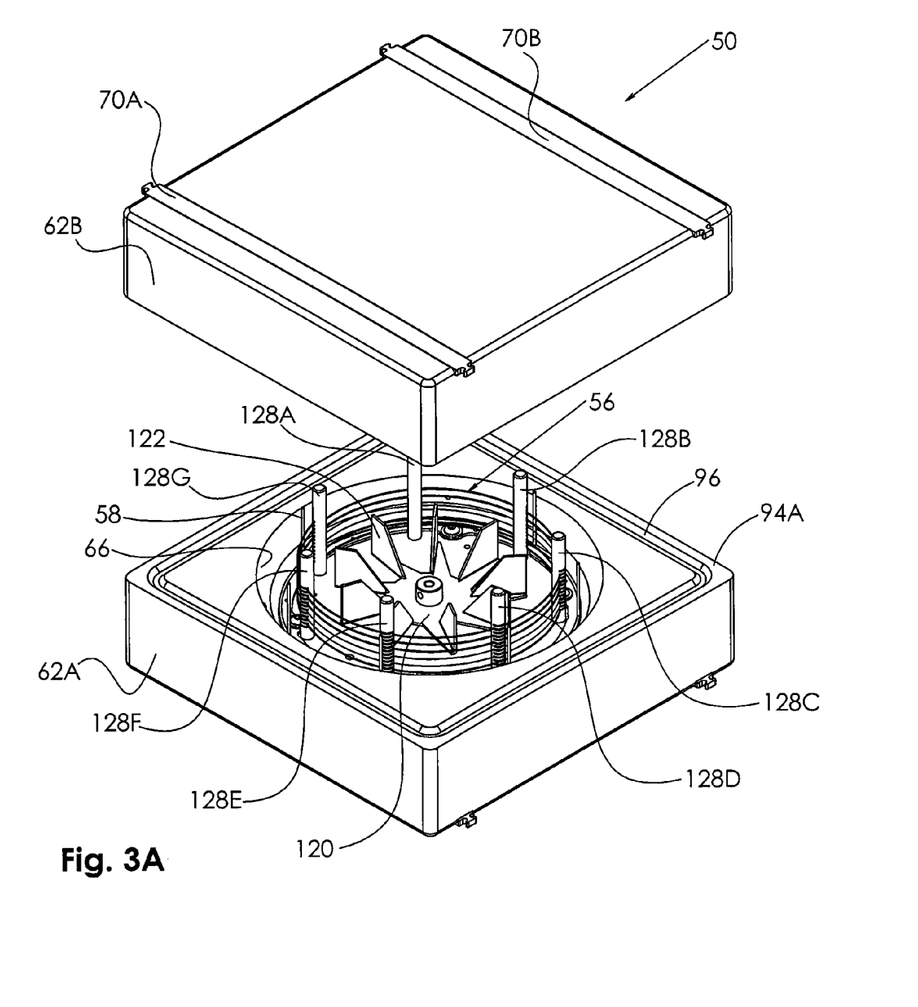
FIGS. 3A and 3B are exploded perspective views of the embodiment of the oven illustrated in FIG. 2.
Figure 3B:
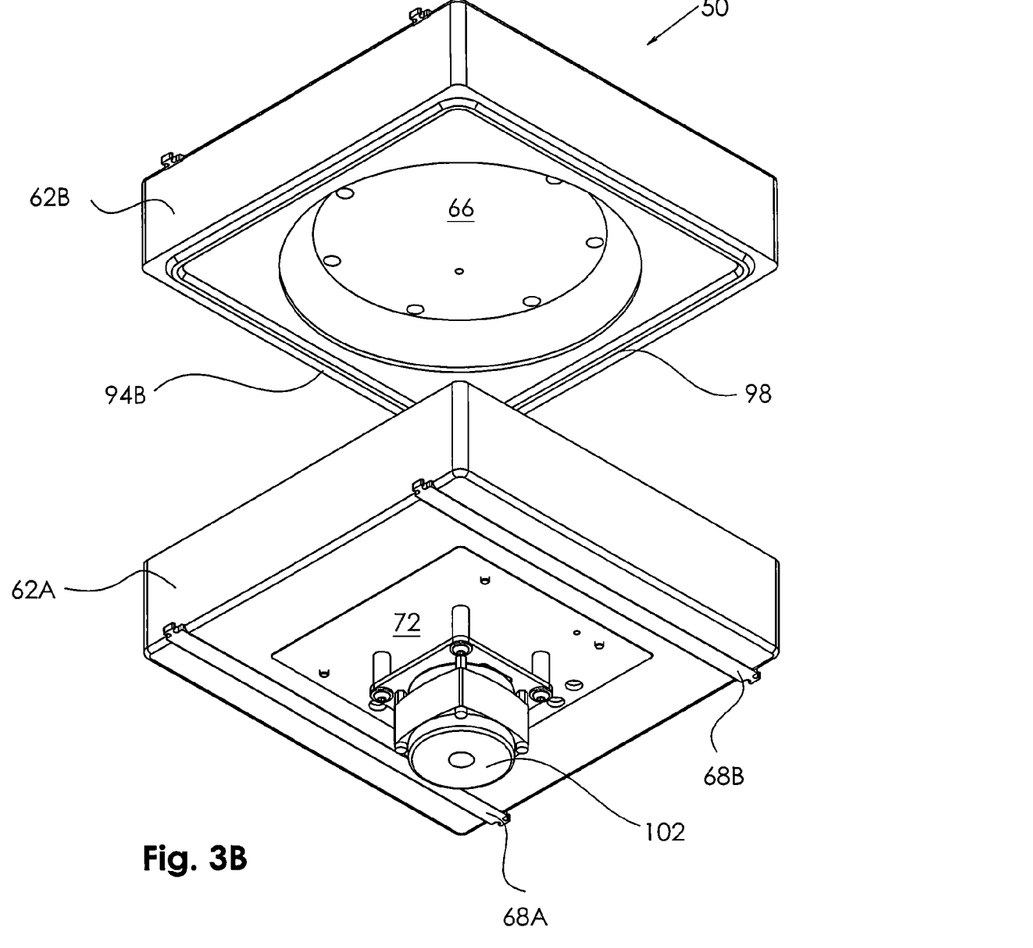
Figure 3C:
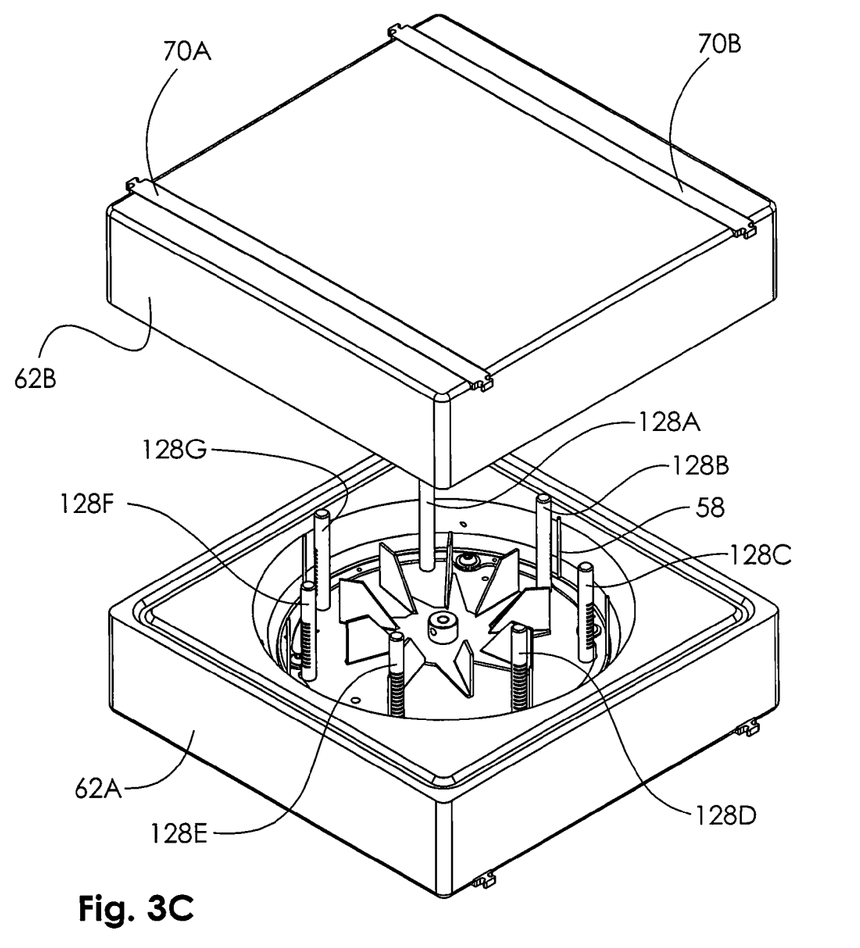
FIG. 3C is an exploded perspective view of the embodiment of the oven illustrated in FIG. 2 with the heating element removed.
Figure 3D:
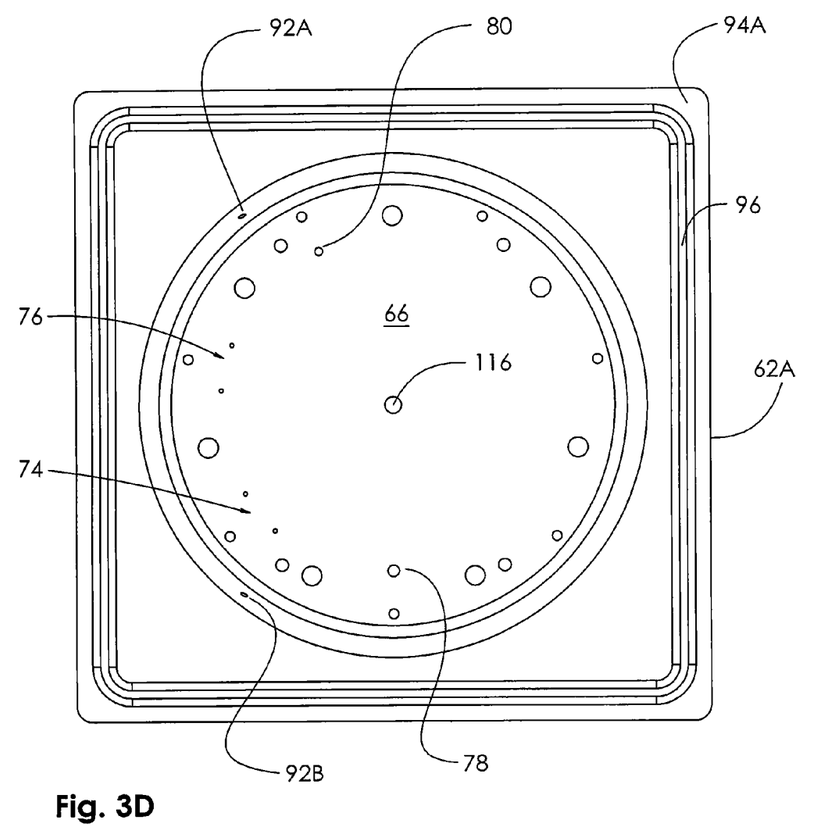
FIG. 3D is a plan view of the interior of the bottom portion of the housing of the oven shown in FIG. 2.

The housing 52 is comprised of a first portion 62A and a second portion 62B that when joined together define an exterior surface 64 and an interior surface 66. Straps 68A, 68B are associated with the exterior surface of the first portion 62A of the housing and the straps 70A, 70B are associated with the second portion 62B of the housing. The straps 68A, 68B and straps 70A, 70B provide surfaces that can be engaged by buckles or other fastening devices to securely join the first and second portions 62A, 62B to one another. The straps can also be used to facilitate the mounting of the housing in a chassis that supports the housing and other elements of a gas chromatograph. Also associated with the exterior surface 64 of the housing is a plate 72 that serves as a mounting surface for a portion of the radial fan 54. The plate 72 also provides a connection interface for providing electricity to the heating element 56 that is substantially located within the interior chamber, receiving air temperature data from a temperature sensor (typically, a platinum resistance thermometer) located in the interior chamber, an inlet port that is used to allow ambient air to enter the interior chamber, and a outlet port that is used to allow air out of the interior chamber. More specifically, the plate 72 supports an electrical plug interface 74 for providing electricity to the heating element 56, an electrical plug interface 76 for the temperature sensor, and pneumatic couplers 78 and 80 respectively associated with the inlet and outlet ports. The pneumatic couplers 78, 80 are used to operatively engage an actuator that is used by the controller of the gas chromatograph to open and close the ports to achieve a desired temperature within the interior chamber.

Figure 5:
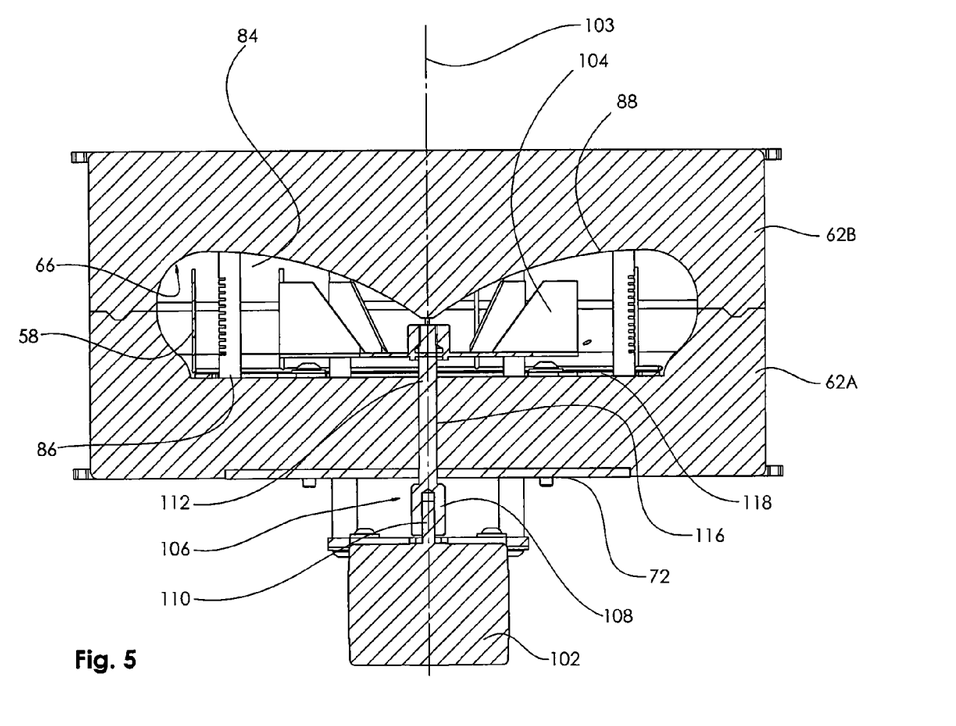
FIG. 5 is cross-sectional view of the embodiment of the oven illustrated in FIG. 2 with the heating element removed.
Figure 6:
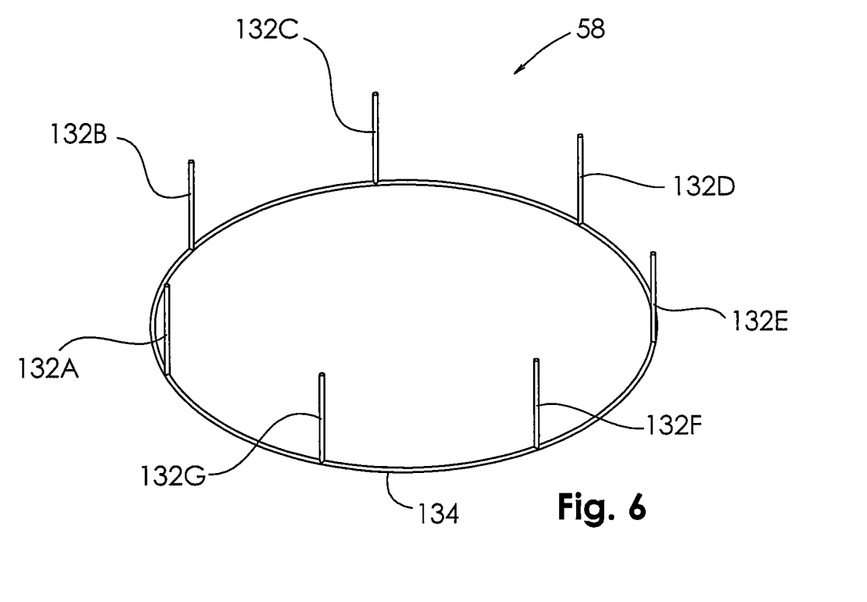
FIG. 6 illustrate a separation column mount suitable for use in the embodiment of the oven illustrated in FIG. 2.

The interior surface 66 of the housing 52 defines an interior chamber 84 that facilitates heat transfer to a sample entrained within a carrier gas traveling through a separation column that is located in the chamber 84 when the oven 50 is in operation. With reference to FIG. 5, the interior surface 66 is comprised of a substantially flat and circular surface 86 and a curved surface 88. The surface 86 provides an attachment surface for a portion of the radial fan 54 and other components located within the chamber 84. The curved surface 88 engages or interacts with the air from the output by the radial fan 54, that is traveling substantially perpendicular to the axis of rotation of the fan blade, and has already past the separation column such that a substantial portion of the air is directed back towards the input or intake portion of the radial fan 54. In the illustrated embodiment, the curved surface operates to direct most of the air that has passed the separation column back towards the input or intake portion of the fan 54. The curved surface, in cross-section, has a butterfly wing type of shape. It should be appreciated that other curved surfaces with shapes different from the illustrated butterfly wing type of shape can be utilized to direct a substantial portion of the air back towards the intake portion of the fan 54.

Figure 4:
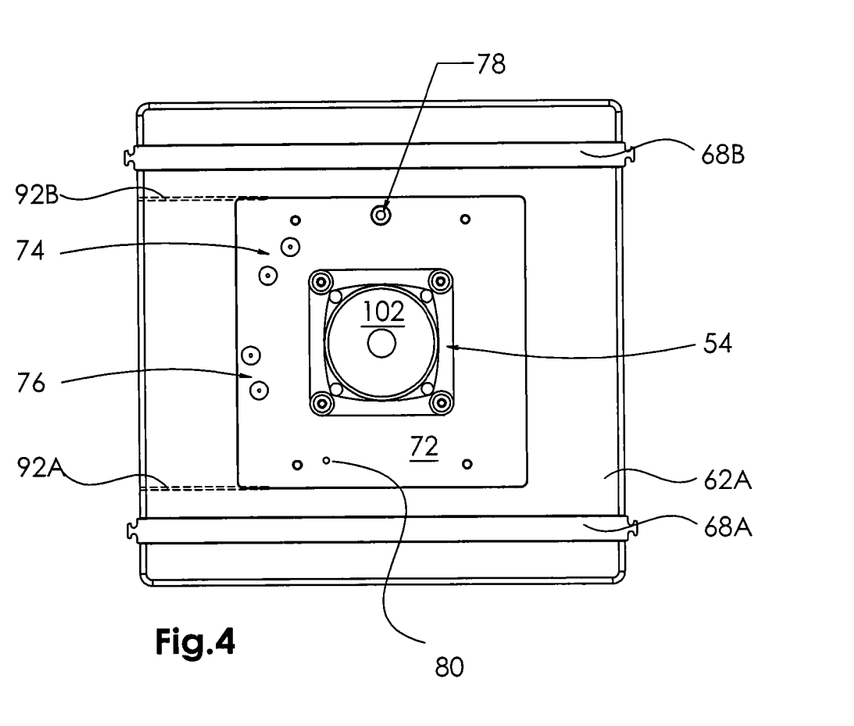
FIG. 4 is a plan view of the surface of the embodiment of the oven illustrated in FIG. 2 on to which an electric motor is mounted.

Extending between the exterior surface 64 and the interior surface 66 of the first portion 62A of the housing 52 are the inlet port, outlet port, the electrical conductors associated with the heating element, and electrical conductors associated with the temperature sensor. With reference to FIG. 4, also extending between the exterior surface 64 and interior surface 66 are column interface ports 92A, 92B that are used to connect the inlet and outlet sections of a separation column located in the interior chamber to the carrier gas circuit, one port for receiving the carrier gas stream and entrained sample and the other port for providing the carrier gas stream and sample to a detector after the stream has passed through a separation column.

Interface surfaces 94A, 94B respectively extend between the portions of the interior and exterior surfaces associated with the first and second portions 62A, 62B of the housing 52. A trough 96 is associated with the interface surface 94A and a corresponding ridge 98 is associated with the interface surface 94B. The trough 96 and ridge 98 serve to align the first and second sections of the 62A, 62B and, if the sections are properly aligned with one another and engaged with one another, deter the escape of air from the interior chamber 84 when the oven is operational.

The first and second portions 62A, 62B of the housing 52 are made of a refractory material that has a low thermal conductivity, preferably less than about 0.2 W·m$^{-1}$·K$^{-1}$. The use of such a material presents a high resistance to the transfer of heat from the air in the interior chamber 52 of the oven 50 to the housing 52 when the oven is in operation. In contrast, one of the purposes of a separation column is to transfer heat to the carrier gas and sample that are passing through the column. As such, separation columns are made from materials with high thermal conductivity and present a low resistance to the transfer of heat from the air in the interior chamber 52 of the oven 50 to the column when the oven is in use. In this regard, many separation columns are made from quartz. By making both the first and second portions 62A, 62B of the housing 52 from a refractory material with low thermal conductivity, there is high resistance to the transfer of heat from air in the chamber 84 across the interior surface 66 that defines the chamber 84, through the first and second portions 62A, 62B, and then across the exterior surface 64 to the ambient atmosphere. As a consequence, heat transfer from the air in the chamber 84 is more likely to occur over a path of lower resistance, such as from the air to separation column.

The refractory material used to make the first and second portions 62A, 62B of the housing 52 is also a refractory material of a type that is capable of being machined or milled to attain curved surfaces, such as the curved surface 88. Exemplary of refractory materials that present a low thermal conductivity and are capable of being machined or milled to produce the relatively complex surfaces, such as the curved surface 88, are thermal fibreboard and ceramic. It is also feasible make the first and second portions 62A, 62B by casting or molding, rather than machining or milling. In this regard, moldable sheet refractory, i.e., fiber reinforced refractory laminate, and other materials known to those skilled in the art can be used in a molding or casting process to produce the first and second portions 62A, 62B.

The radial fan 54 operates to produce a stream of air within the interior chamber 84 that is substantially perpendicular to the axis of rotation of the fan blade, i.e., a stream of air that is radially directed relative to the axis of rotation. The fan 54 is comprised of an electric motor 102, a fan blade 104, and a drive shaft 106 that connects the motor 102 to the fan blade and that defines an axis of rotation 103 of the fan blade 104. The electric motor 102 is mounted on a pedestal that is attached to the plate 72 associated with the first portion 62A of the housing 52. With reference to FIG. 5, the drive shaft 106 extends from a first end 108 that engages a rotor 110 of the motor 102 to a second end 112 that engages the fan blade 104 at a hub 114. The drive shaft 106 partially resides in a hole 116 defined by the first portion 62A of the housing, the plate 72 associated with the exterior surface 64, and a plate 118 attached to the surface 86. The plates 72 and 118 support the drive shaft 106 such that the shaft is substantially perpendicular to the surface 86. The fan blade 104 is comprised the hub 114, a base 120 that extends substantially perpendicular to the axis of rotation 103, and a group of fins 122 that extend substantially perpendicular to the base 120.

It should be appreciated that the invention is not limited to the particular radial fan depicted in the drawings. Other radial fans, such as a squirrel cage fan, are also feasible. Further, the invention is not limited to the use of an electrical motor positioned as shown in the drawings. An electrical motor can be located elsewhere and a transmission system comprised of well known elements in the art (e.g., gears, screws, or pulleys etc.) used to transmit the rotational energy produced by the motor to a fan blade located within the interior chamber 84.

The heating element 56 is comprised of an electrical wire that, in operation, attains a temperature that is dependent on the amount of current being applied to the wire. The wire is comprised of a wound section 126 that is located within the interior chamber 84 and is used to produce the heat that is to be transferred to separation column. Typically, the wire is a nickel-chromium alloy. However, heater wires made of other materials are also feasible. The wire is further comprised of a pair of leads that extend from the wound section 126 through the first portion 62A of the housing 52 to plug 74.

The wound section 126 preferably is in the form of a circular helix. The axis of the helix, i.e., the axis of a circular cylinder that the wire can be conceptualized as wrapping around, is substantially coincident with the axis of rotation 103 of the radial fan blade 104. Further, the radius of the helix, i.e., the radius of the circular cylinder that the wire can be conceptualized as wrapping around, is greater than the radius of the fan blade 104. As such, the radial distance between the end of the fan blade 104 and the wound section 126 of the heating element 56 is substantially constant. Further, the wound section 126 is positioned to receive air from the radial fan 54 that is moving in a direction that is substantially perpendicular to the axis of rotation 103 of the fan blade 104. The pitch between the windings in the wound section 126 is large enough to allow a substantial portion of the air being received from the fan to pass between the windings and small enough so that significant heat transfer can occur between the windings and the passing air. In the illustrated embodiment, the wire typically is 18-26 gauge and the pitch typically is in the range of 0.1-0.25 inches, thereby producing a gap between consecutive windings in the range of 0.1-0.25 inches. The pitch between windings is maintained by notched posts 128A-128G, each of which is attached to and extends from the plate 118. Each notch in a post retains a portion of a winding and maintains the separation or pitch of the winding relative to the winding retained by the next notch on the post. The posts 128A-128G are each made of a material or materials that have a low thermal conductivity, thereby promoting the transfer of heat to the separation column and not to the posts. In the illustrated embodiment, the posts 128A-128G are each made of a low thermal conductivity ceramic with a threaded end that engages a tapped hole in the plate 118. The wire can be straight wire that is manipulated to achieve the curve of the desired helix shape and engage the posts 128A-128G. Alternatively, the wire can be pre-curved and, as such, not need to be manipulated to achieve the curve of the desired helix shape.

It should be appreciated that while the wound section 126 of the heating element is preferably in the form of a circular helix, a wound section with a polygonal helix is also possible. For instance, if the windings follow substantially straight lines between each of the notched posts 128A-128G, a heptagonal helix is produced. Such helixes, however, result in the radial distance between the fan blade 104 and the wound section varying instead of being substantially constant. This may lead to a radially dependent variation in the heat transfer to a separation column. However, any such variation may be insignificant or otherwise acceptable in certain circumstances. The wound section can also be a helix having a side comprised of one or more curved sections and one or more straight sections. Such a helix will also result in the radial distance between the fan blade and the wound section varying.

The oven 50 has a relatively low profile. More specifically, the dimension of the oven in the direction of the drive shaft 106 is relatively small. This is, in part, attributable to the dimension of the interior chamber 84 in the direction of the drive shaft 106 being relatively small and no more than about twice the greater of the height of the fan blade 104 and the height of the helically wound section 126 in the direction of the drive shaft 106.

The separation column mount 58 serves to position the wound section of a separation column that is in the form of a circular helix to receive air from the radial fan 54 that is moving in a direction substantially perpendicular to the axis of rotation of the fan blade 104. The separation column mount 58 is comprised of a series of posts 132A-132G attached to a ring 134 that is, in turn, attached to the plate 118. The mount 58 also serves to position the wound section of a separation column such that the axis of the helix is substantially coincident with the axis of rotation 103 of the radial fan blade 104. As such, the radial distance between the end of the fan blade 104 and the wound section of the separation column is substantially constant. Likewise, the radial distance between the wound section 126 of the heating element 56 and the wound section of the separation column is substantially constant.

It should be appreciated that a number of separation column mounts other than the mount 58 are feasible. For instance, a mount comprised of one or more clips is feasible. Another possibility is a seat on the interior surface of the housing in which a portion of the separation column resides and that provides the necessary positioning for the wound section of the separation column. If the separation column is relatively rigid, the orientation of one or both of the connecting elements commonly associated with an oven and that engage the mating, connecting elements associated with the separation column can be used to achieve the necessary positioning of the wound section of the separation column within the interior chamber of the oven. It should also be appreciated that, if the wound section of a separation column is in a form other than a circular helix (e.g., a polygonal helix), a separation column mount can be adapted to accommodate the different shape.

The operation of the oven 50 in heating a separation column and the carrier gas and entrained sample being borne by the column is now discussed. Assuming that the oven 50 does not contain a separation column, the first and second portions 62A, 62B of the housing 52 are separated from one another and a separation column appropriate for the particular analysis being conducted is positioned in the interior chamber 84 using the separation column mount 58. The inlet section of the column is also connected so as to receive a carrier gas and entrained sample. Similarly, the outlet section of the column is connected so as to provide the carrier gas and entrained sample to a detector. After the separation column has been established in the interior chamber 84, the first and second portions 62A, 62B of the housing are brought together. The oven 50 is now in condition to be used in the analysis of a sample by a gas chromatograph. A carrier gas and sample entrained in the carrier gas are received by the separation column in the interior chamber 84 of the oven. Typically, the flow of the carrier gas, injection of the sample into the carrier gas stream, and the providing of the carrier gas stream with the entrained sample are initiated by the controller of the gas chromatograph. In any event, once the carrier gas and sample begin to pass through the separation column, the oven 50 is operated so as to subject the separation column, carrier gas, and sample to a particular temperature profile. For the transfer of heat from the wound section 126 of the heating element to the separation column, carrier gas, and sample, the inlet port is closed to prevent ambient air from entering the interior chamber 84 and the outlet port is closed to prevent air that is in the chamber 84 from exiting the chamber 84. Typically, the closing of the inlet and outlet ports is initiated by the controller of the gas chromatograph enabling one or more actuators to close the ports. With the first and second sections 62A, 62B of the housing joined and the inlet and outlet ports closed, there is a substantially fixed volume of air in the interior chamber 84. It should be appreciated that the radial positioning of the radial fan 54, wound section 126 of the heating element 56, and a separation column as determined by the separation column mount 58, allowed the interior chamber 84 to have a relatively small volume. This small volume means that there is less air in the interior chamber 84 to heat than in a larger chamber, everything else being equal. As such, the transfer of heat from the air to the separation column can be accomplished more quickly than in ovens with larger internal chambers.

Figure 7:
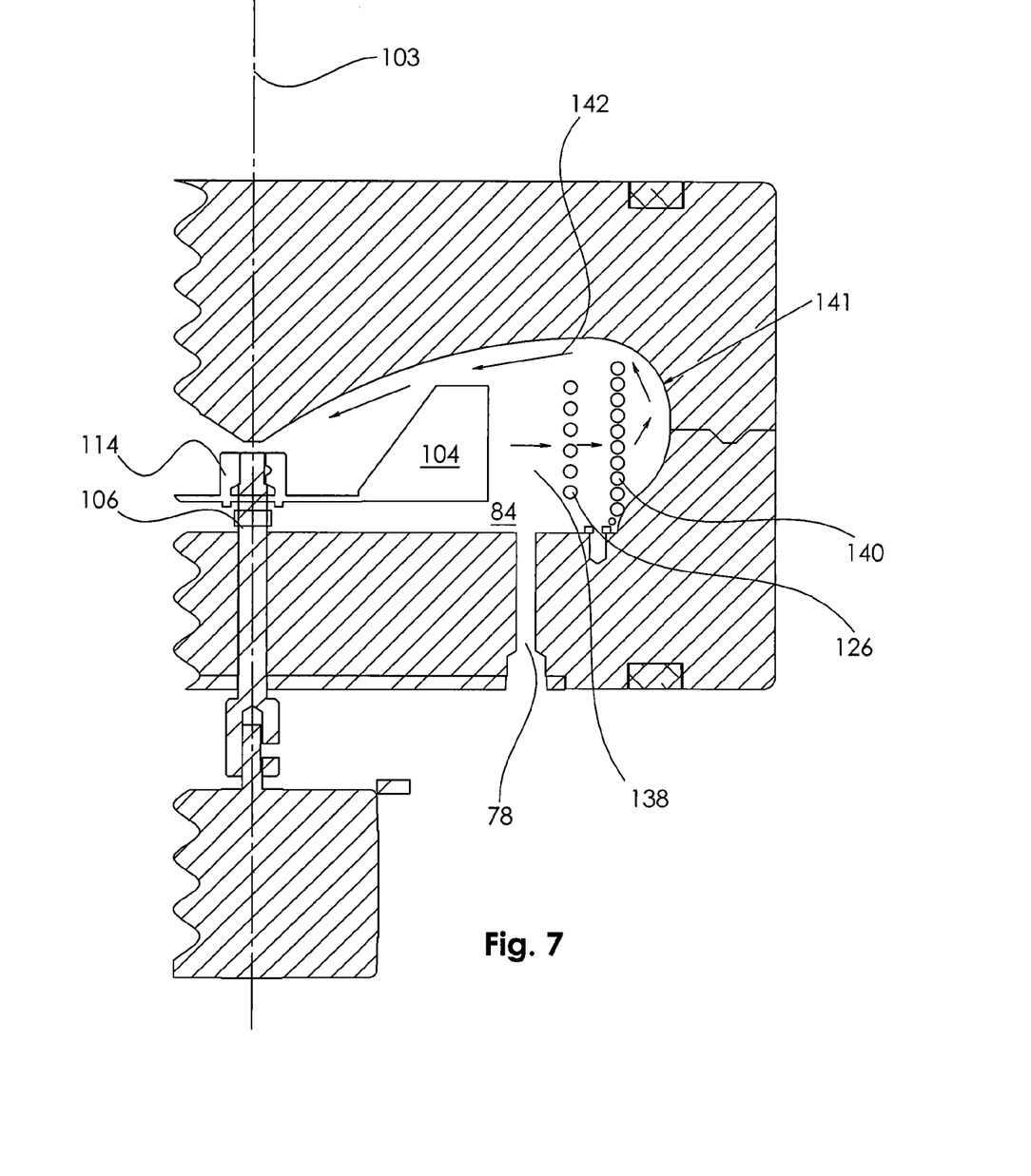
FIG. 7 schematically depicts the air flow used to transfer heat from the heating element to a separation column within the interior chamber of the oven illustrated in FIG. 2 and with the posts that support the heating element and the separation column mount removed.

Heat transfer to the separation column commences with the application of current to the heating element 56, which results in the wound section 126 increasing in temperature, and the activation of the radial fan 54. The application of current to the heating element 56 and the activation of the fan 54 are typically initiated by the controller of the gas chromatograph. With reference to FIG. 7, the rotation of the fan blade 104 causes air in the chamber 84 that is adjacent to the center of the blade 104 (i.e., adjacent to the intake portion of the fan) to be drawn toward the blade 104 and subsequently pushed away from the outer edge of the blade 104 in a direction that is substantially perpendicular to the axis of rotation 103 of the blade 104 (i.e., in the direction of arrow 138). The air that is leaving the blade 104 subsequently engages the wound section 126 of the heating element 56 and heat is transferred from the wound section 126 to the air. The heated air, which is still moving substantially perpendicular to the axis of rotation of the blade, then engages the helically wound section 140 of the separation column and heat is transferred from the air to the separation column. Subsequently, heat is transferred from the column to the carrier gas and entrained sample passing through the column. After passing the separation column, the air is still moving substantially perpendicular to the axis of rotation of the blade. This air is deflected by a side wall 141 of the curved surface 88, i.e., the portion of the curved surface facing the portion of the air stream that is traveling substantially perpendicular to the axis of rotation of the blade, such that the air substantially follows a path denoted by arrow 142 back toward the center of the blade 104 to be recirculated by the operation of the blade 104.

The controller of the gas chromatograph uses the temperature data provided by the temperature sensor located in the interior chamber 84 to regulate the heat transfer. Such regulation may involve the increasing or decreasing of current to the wound section of the heating element 56, increasing or decreasing the speed of the fan blade 104, and/or opening or closing one or both of the inlet and outlet ports to regulate the exchange of air between the ambient atmosphere and the interior chamber 84.

It should be appreciated that, while the wound section 126 of the heating element 56 is positioned between the fan blade 104 and a separation column that is positioned by the separation column mount 58, the locations of the wound section 126 and the separation column mount 58 could be reversed so that the separation column would be positioned between the fan blade 104 and the wound section 126 of the heating element 56. Such an arrangement would result in the air that the fan blade 104 is causing to move in a direction that is substantially perpendicular to the axis of rotation 103 of the blade 104 to engage the wound section of the separation column before engaging the wound section 126 of the heating element 56. Consequently, air heated by the wound section 126 would have to travel along path 142 to the inlet of the blade 104 and then pushed by the operation of the blade into engagement with the separation column. This arrangement is likely to result in some heat transfer from the air to the first portion 62A of the housing 52 as the heated air travels along the path 142. However, due to the low thermal conductivity of the material used for the first portion 62A of the housing 52, any such heat transfer may be relatively small or otherwise acceptable in certain instances.

While the invention has been described with reference to a preferred embodiment, it will be understood by those skilled in the art that various other changes in form and details may be made without departing from the spirit and scope of the invention.

What is claimed is:

1. An oven for use in a gas chromatograph device, the oven comprising:
 a housing with an exterior surface and an interior surface that defines an interior chamber;
 a radial fan comprising a drive shaft and a fan blade operatively connected to the drive shaft, the radial fan, when in operation, driving air in a direction that is substantially perpendicular to the drive shaft, the fan blade and at least a portion of the drive shaft being located within said interior chamber;
 a heating element for heating air within the interior chamber, a substantial portion of the heating element positioned to receive, when in operation, air that is being driven by the radial fan in a direction that is substantially perpendicular to the drive shaft of the radial fan; and a separation column mount for positioning a substantial portion of a separation column to receive, when in operation, air that is being driven by the radial fan in a direction that is substantially perpendicular to the drive shaft of the radial fan;

wherein the substantial portion of the heating element is located between the fan blade and the location at which the separation column mount would hold the substantial portion of the separation column.

2. An oven, as claimed in claim 1, wherein:
the substantial portion of the heating element comprises wire wound in a circular helix.

3. An oven, as claimed in claim 1, wherein:
the interior surface comprises a substantially flat surface that is made from a refractory material.

4. An oven, as claimed in claim 1, wherein:
said interior surface of said housing is entirely made of a refractory material.

5. An oven, as claimed in claim 1, wherein
the housing from the interior surface to the exterior surface comprises a refractory material.

6. An oven for use in a gas chromatograph device, the oven comprising:
a housing with an exterior surface and an interior surface that defines an interior chamber;
a radial fan comprising a drive shaft and a fan blade operatively connected to the drive shaft, the radial fan, when in operation, driving air in a direction that is substantially perpendicular to the drive shaft, the fan blade and at least a portion of the drive shaft being located within said interior chamber;
a heating element for heating air within the interior chamber, a substantial portion of the heating element positioned to receive, when in operation, air that is being driven by the radial fan in a direction that is substantially perpendicular to the drive shaft of the radial fan; and
a separation column mount for positioning a substantial portion of a separation column to receive, when in operation, air that is being driven by the radial fan in a direction that is substantially perpendicular to the drive shaft of the radial fan;
wherein the location at which the separation column mount would hold the substantial portion of the separation column is located between the fan blade and the substantial portion of the heating element.

7. An oven, as claimed in claim 6, wherein:
the substantial portion of the heating element comprises wire wound in a circular helix.

8. An oven, as claimed in claim 6, wherein:
the fan blade has a fan blade height in the direction of the drive shaft;
the portion of the heating element has a heating element height in the direction of the drive shaft; and
the interior chamber has a maximum height in the direction of drive shaft that is less than about two times the greater of the fan blade height and the heating element height.

9. An oven, as claimed in claim 6, wherein:
the interior surface comprises a side surface for engaging, when in operation, air that is being driven by the radial fan in a direction that is substantially perpendicular to the drive shaft of the radial fan, the side surface being curved so as to redirect engaged air along a path that returns the engaged air to an intake portion of the radial fan.

10. An oven, as claimed in claim 9, wherein:
the side surface is made from a refractory material.

11. An oven, as claimed in claim 6, wherein:
the interior surface comprises a substantially flat surface that is made from a refractory material.

12. An oven, as claimed in claim 6, wherein:
said interior surface of said housing is entirely made of a refractory material.

13. An oven for use in a gas chromatograph device, the oven comprising:
a housing with an exterior surface and an interior surface that defines an interior chamber;
a radial fan comprising a drive shaft and a fan blade operatively connected to the drive shaft, the radial fan, when in operation, driving air in a direction that is substantially perpendicular to the drive shaft, the fan blade and at least a portion of the drive shaft being located within said interior chamber;
a heating element for heating air within the interior chamber, a substantial portion of the heating element positioned to receive, when in operation, air that is being driven by the radial fan in a direction that is substantially perpendicular to the drive shaft of the radial fan; and
a separation column mount for positioning a substantial portion of a separation column to receive, when in operation, air that is being driven by the radial fan in a direction that is substantially perpendicular to the drive shaft of the radial fan;
the fan blade has a fan blade height in the direction of the drive shaft;
the portion of the heating element has a heating element height in the direction of the drive shaft; and
the interior chamber has a maximum height in the direction of drive shaft that is less than about two times the greater of the fan blade height and the heating element height.

14. An oven for use in a gas chromatograph device, the oven comprising:
a housing with an exterior surface and an interior surface that defines an interior chamber;
a radial fan comprising a drive shaft and a fan blade operatively connected to the drive shaft, the radial fan, when in operation, driving air in a direction that is substantially perpendicular to the drive shaft, the fan blade and at least a portion of the drive shaft being located within said interior chamber;
a heating element for heating air within the interior chamber, a substantial portion of the heating element positioned to receive, when in operation, air that is being driven by the radial fan in a direction that is substantially perpendicular to the drive shaft of the radial fan; and
a separation column mount for positioning a substantial portion of a separation column to receive, when in operation, air that is being driven by the radial fan in a direction that is substantially perpendicular to the drive shaft of the radial fan;
wherein the interior surface comprises a side surface for engaging, when in operation, air that is being driven by the radial fan in a direction that is substantially perpendicular to the drive shaft of the radial fan, the side surface being curved so as to redirect engaged air along a path that returns the engaged air to an intake portion of the radial fan.

15. An oven, as claimed in claim 14, wherein:
the side surface is made from a refractory material.

16. An oven for use in a gas chromatograph device, the oven comprising:
a housing with an exterior surface and an interior surface that defines an interior chamber;
a radial fan comprising an electric motor with a drive shaft and a fan blade operatively connected to the drive shaft, the radial fan, when in operation, driving air in a direction that is substantially perpendicular to the drive shaft, the fan blade and at least a portion of the drive shaft being located within said interior chamber, the fan blade having a first radius relative to the drive shaft;

a heating element for heating air within the interior chamber, a portion of the heating element comprising a wire wound in a circular helix and positioned to receive, when in operation, air that is being driven by the radial fan in a direction that is substantially perpendicular to the drive shaft of the radial fan; and a separation column mount for positioning a portion of a separation column that comprises a tube wound in a circular helix to receive, when in operation, air that is being driven by the radial fan in a direction that is substantially perpendicular to the drive shaft of the radial fan;

the wire wound in a circular helix has a second radius;

the separation column mount for positioning a tube wound in a circular helix that has a third radius; and the third radius is greater than the second radius.

17. An oven, as claimed in claim 16, wherein:
the interior surface comprises a substantially flat surface that is made from a refractory material.

18. An oven for use in a gas chromatograph device, the oven comprising:

a housing with an exterior surface and an interior surface that defines an interior chamber;

a radial fan comprising an electric motor with a drive shaft and a fan blade operatively connected to the drive shaft, the radial fan, when in operation, driving air in a direction that is substantially perpendicular to the drive shaft, the fan blade and at least a portion of the drive shaft being located within said interior chamber, the fan blade having a first radius relative to the drive shaft;

a heating element for heating air within the interior chamber, a portion of the heating element comprising a wire wound in a circular helix and positioned to receive, when in operation, air that is being driven by the radial fan in a direction that is substantially perpendicular to the drive shaft of the radial fan; and a separation column mount for positioning a portion of a separation column that comprises a tube wound in a circular helix to receive, when in operation, air that is being driven by the radial fan in a direction that is substantially perpendicular to the drive shaft of the radial fan;

the wire wound in a circular helix has a second radius;

the separation column mount for positioning a tube wound in a circular helix that has a third radius; and the second radius is greater than the third radius.

19. An oven for use in a gas chromatograph device, the oven comprising:

a housing with an exterior surface and an interior surface that defines an interior chamber;

a radial fan comprising an electric motor with a drive shaft and a fan blade operatively connected to the drive shaft, the radial fan, when in operation, driving air in a direction that is substantially perpendicular to the drive shaft, the fan blade and at least a portion of the drive shaft being located within said interior chamber, the fan blade having a first radius relative to the drive shaft;

a heating element for heating air within the interior chamber, a portion of the heating element comprising a wire wound in a circular helix and positioned to receive, when in operation, air that is being driven by the radial fan in a direction that is substantially perpendicular to the drive shaft of the radial fan; and a separation column mount for positioning a portion of a separation column that comprises a tube wound in a circular helix to receive, when in operation, air that is being driven by the radial fan in a direction that is substantially perpendicular to the drive shaft of the radial fan;

the interior surface comprises a side surface for engaging, when in operation, air that is being driven by the radial fan in a direction that is substantially perpendicular to the drive shaft of the radial fan, the side surface being curved so as to redirect engaged air along a path that returns the engaged air to the intake portion of the radial fan.

20. An oven, as claimed in claim 19, wherein:
the side surface is made from a refractory material.

* * * * *